(12) United States Patent
Lees (10) Patent No.: US 6,585,973 B1
(45) Date of Patent: Jul. 1, 2003

(54) METHOD FOR PREPARING SOLID PHASE CONJUGATED VACCINE

(75) Inventor: Andrew Lees, Silver Spring, MD (US)

(73) Assignee: Henry M. Jackson Foundation for The Advancement of Military Medicine, Rockville, MD (US)

(*) Notice: Subject to any disclaimer, the term of this patent is extended or adjusted under 35 U.S.C. 154(b) by 0 days.

(21) Appl. No.: 09/428,498

(22) Filed: Oct. 28, 1999

Related U.S. Application Data (60) Provisional application No. 60/106,090, filed on Oct. 29, 1998.

(51) Int. Cl.$^7$ .................................. A61K 39/385
(52) U.S. Cl. ..................... 424/193.1; 424/194.1; 424/196.11; 424/197.11
(58) Field of Search ............... 424/193.1, 194.1, 424/197.11, 196.11

(56) References Cited

U.S. PATENT DOCUMENTS

| | | |
|---|---|---|
| 5,585,100 A | 12/1996 | Mond et al. |
| 5,651,971 A | 7/1997 | Lees |
| 5,693,326 A | 12/1997 | Lees |
| 5,955,079 A | 9/1999 | Mond et al. |

FOREIGN PATENT DOCUMENTS

| | | |
|---|---|---|
| WO | WO 96/40239 | 12/1996 |
| WO | WO 97/00697 | 1/1997 |
| WO | WO 98/30239 | 7/1998 |

OTHER PUBLICATIONS

Cruse, J.M. et al. Eds., *Conjugate Vaccines* pp. 48–114 (1989).
Lees, A. et al. *Vaccine* 14:3, pp. 190–198 (1996).
Peeters, C. et al. *Vaccine* vol. 10, pp. 833–840 (1992).
Houen, G. et al. *J. Immunological Methods* vol. 206, pp. 125–134 (1997).
Al–Shakhshir, R.H. et al. *Vaccine* 13:1, pp. 41–44 (1995).
Rinella, Jr., J.V. et al. *Vaccine* 14:4, pp. 298–300 (1996).
Chang, M. et al. *PDA J. Pharm. Science & Technology* 51:1, pp. 25–29 (1997).
Lees et al. *Vaccine* 12:13, pp. 1160–1166 (1994).
Wallick, S. et al. *J. Immunol* 130:6, pp. 2871–2875 (Abstract Only) (1983).
McDaniel, L.S. et al. *J. Immunol.* 133:6, pp. 3308–3312 (Abstract Only) (1984).
Briles, D.E. et al. *Infect Immun.* 60:5, pp. 1957–1962 (Abstract Only) (1992).
LaFerriere, C.A. et al. *Vaccine* 15:2, pp. 179–186 (1997).
Wu, H.Y. et al. *J. Infec. Dis.* 175:4, pp. 839–846 (Abstract Only) (1997).
Wortham, C. L. et al. *Infection and Immunity* 66:4, pp. 1513–1520 (1998).
Monsigny, M. et al. *Analytical Biochemistry* vol. 175, pp. 525–530 (1988).
Spande, T.F. *J. Org. Chem*, vol. 45, pp. 3081–3084 (1980).
Ames, B.N. et al. *J. Biol. Chem.* 235:3, pp. 769–775 (1960).
Lindsberg, M.L. et al. *J. Immun.* 147:11, pp. 3774–3779 (1991).
Snapper, C. M. et al. *J. Exper. Med.* vol. 175, pp. 1367–1371 (1992).
Pecanha, L. M. et al. *J. Immun.* vol. 150, pp. 3215–3223 (1993).
Snapper, C.M. et al. *Journal Immunology* 150:7, pp. 2737–2745 (1993).
Mond, J.J. et al. *Ann Rev. Immunol.* vol. 13, pp. 655–692 (1995).
Mond, J.J. et al. *Current Opinion in Immunology* vol. 7, pp. 349–354 (1995).
Campbell, K. A. et al. *Eur. J. Immun.* vol. 22, pp. 2107–2112 (1992).
Squire, C.M. et al. *J. Immun.* vol. 152, pp. 4388–4396 (1994).
Campbell, K.A. et al. *International Immunology* 9:8, pp. 1131–1140 (1997).
Lees, A. et al. *J. Immun.* 145:11, pp. 3594–3600 (1990).
Morris, S.C. et al. *J. Immun.* vol. 152, pp. 3777–3785 (1994).
Finkelman, F.D. et al. *J. Immun.* vol. 157, pp. 1406–1414 (1996).
Cassels, F.J. et al. *J. Indus. Microbiol. & Biotech.*vol. 19, pp. 66–70 (1997).
Fischer, G.W. et al. *J. Infect. Dis.* 169:2, pp. 324–329 (Abstract Only) (1994).
Kossovsky, N. et al., *Bioconjugate Chem.* 6:5, pp. 507–520 (1995).
Anderson P.W. et al. *J. Immunol.* 142:7, pp. 2464–2468 (Abstract Only) (1989).
R.K. Gupta, et al. *Vaccine* 11:3, pp. 293–306 (1993).
Lees et al., *Abstract for 11$^{th}$ International Pathogen. Neisseria Conference*, Nice, France, p. 161 (1998).
McKee, M. L. et al. *Infection and Immunity* 64:6, pp. 2225–2233 (1996).
Frey et al., *Bioconjugate Chem.* vol. 8, pp. 424–433 (1997).

*Primary Examiner*—Patrick J. Nolan
*Assistant Examiner*—Gerald R. Ewoldt
(74) *Attorney, Agent, or Firm*—Finnegan, Henderson, Farabow, Garrett, & Dunner, L.L.P.

(57) ABSTRACT

A method of preparing conjugate vaccines by adsorbing a protein to a solid phase adjuvant, and covalently linking a carbohydrate to the adsorbed protein. Alternatively, the carbohydrate is first adsorbed to the solid phase adjuvant, then the protein is covalently linked to the carbohydrate. The carbohydrate may be chemically activated. Unconjugated protein may be present.

10 Claims, 4 Drawing Sheets

METHOD FOR PREPARING SOLID PHASE CONJUGATED VACCINE

This application claims the benefit under 35 U.S.C. §119(e) of U.S. Provisional Application No. 60/106,090 filed Oct. 29, 1998.

GOVERNMENT INTEREST

The invention described herein may be manufactured, licensed and used for governmental purposes without the payment of any royalties thereon.

BACKGROUND OF THE INVENTION

1. Field of the Invention

The present invention relates to conjugate vaccines. More particularly, the present invention relates to solid phase conjugate vaccines.

2. Description of Related Arts

In the process of vaccination, medical science uses the body's innate ability to protect itself against invading agents by immunizing the body with antigens that will not cause the disease but will stimulate the formation of antibodies that will protect against the disease. For example, dead organisms are injected to protect against bacterial diseases such as typhoid fever and whooping cough, toxins are injected to protect against tetanus and botulism, and attenuated organisms are injected to protect against viral diseases such as poliomyelitis and measles.

It is not always possible, however, to stimulate antibody formation merely by injecting the foreign agent. The vaccine preparation must be immunogenic, that is, it must be able to induce an immune response. Certain agents such as tetanus toxoid are innately immunogenic, and may be administered in vaccines without modification. Other important agents are not immunogenic, however, and must be converted into immunogenic molecules before they can induce an immune response. The immune response is a complex series of reactions that can generally be described as follows: (1) the antigen enters the body and encounters antigen-presenting cells which process the antigen and retain fragments of the antigen on their surfaces; (2) the antigen fragments retained on the antigen presenting cells are recognized by T cells that provide help to B cells; and (3) the B cells are stimulated to proliferate and divide into antibody forming cells that secrete antibody against the antigen.

Most antigens only elicit antibodies with assistance from the T cells and, hence, are known as T-dependent (TD). Examples of such T-dependent antigens are tetanus and diphtheria toxoids.

Some antigens, such as polysaccharides, cannot be properly processed by antigen presenting cells and are not recognized by T cells. These antigens do not require T cell assistance to elicit antibody formation but can activate B cells directly and, hence, are known as T-independent antigens (TI). Such T-independent antigens include *H. influenzae* type b polyribosyl-ribitol-phosphate (PRP) and pneumococcal capsular polysaccharides.

Other differences between T-independent and T-dependent antigens are:

a) T-dependent antigens, but not T-independent antigens, can prime an immune response so that a memory response results on secondary challenge with the same antigen.

b) The affinity of the antibody for antigen increases with time after immunization with T-dependent, but not T-independent antigens.

c) T-dependent antigens stimulate an immature or neonatal immune system more effectively than T-independent antigens.

d) T-dependent antigens usually stimulate IgM, IgG1, IgG2a, and IgE antibodies, while T-independent antigens stimulate IgM, IgG1, IgG2b, and IgG3 antibodies.

T-dependent antigens can stimulate primary and secondary responses which are long-lived in both adult and in neonatal immune systems, but must frequently be administered with adjuvants. Very small proteins, such as peptides, are rarely immunogenic, even when administered with adjuvants.

T-independent antigens, such as polysaccharides, are able to stimulate immune responses in the absence of adjuvants, but cannot stimulate high level or prolonged antibody responses. They are also unable to stimulate an immature or B cell defective immune system (Mond J J., *Immunological Reviews*, 64:99 (1982) (Mosier D E, et al., *J. Immunol.*, 119:1874 (1977). For T-independent antigens, it is critical to provide protective immunity against such antigens to children, especially against polysaccharides such as *H. influenzae* and *S. pneumoniae*. For T-dependent antigens, it is critical to develop vaccines based on synthetic peptides that represent the primary antigenic determinants of various pathogens.

One approach to enhance the immune response to T-independent antigens involves conjugating polysaccharides such as *H. influenzae* PRP (Cruse J M, Lewis R E Jr. ed., *Conjugate Vaccines in Contributions to Microbiology and Immunology*, Vol. 10, (1989) or oligosaccharide antigens (Anderson P W, et al., *J. Immunol.*, 142:2464, (1989) to a single T-dependent antigen such as tetanus or diphtheria toxoid. Recruitment of T cell help in this way has been shown to provide enhanced immunity to many infants that have been immunized.

Protein-polysaccharide conjugate vaccines stimulate an anti-polysaccharide antibody response in infants who are otherwise unable to respond to the polysaccharide alone.

Conjugate vaccines are effective, but expensive to produce. See Cruse. One problem in the preparation of conjugate vaccines is removal of the unconjugated protein from the covalently linked protein. Typically, this is done by size exclusion gel filtration and requires a large and dedicated column. Houen et al. demonstrated that peptides could be coupled to protein adsorbed to solid phase aluminum adjuvants. Houen, G. et al., *J. Immun. Meth.*, 206:125 (1997). Furthermore, they found the anti-peptide antibody response induced by these solid phase conjugates was higher than that induced by conjugates prepared in solution phase. Synthesis of these solid phase conjugates was simple because unconjugated peptide and reagents could be removed by centrifugation of the solid phase components. Importantly, since the solid phase is itself the adjuvant, there was no need for the conjugate to be removed from the solid phase scaffold on which the immunogen was synthesized. This overcomes a significant disadvantage of other solid phase synthetic approaches. But Houen et al. did not address non-peptide applications, e.g., carbohydrates.

Kossovsky discusses "antigen delivery vehicles" made up of a diamond nanoparticle that is coated with cellobiose, a disaccharide, to form a "colloid surface" that would bind to a protein antigen. Kossovsky et al., *Bioconj. Chem.* 6(5), pp. 507–520 (1995). The antigen delivery vehicle serves to present the protein antigen to "evoke a strong immunogenic response" to the protein antigen. It does not seek, and in fact it would be undesirable, to evoke any immunogenic response to the disaccharide, because cellobiose is a repeat unit of cellulose, which is a common food additive.

Thus, there remains a need in the art to simplify the preparation of solid phase dual carrier conjugate vaccines, in particular removal of free hapten, protein and polysaccharide.

SUMMARY OF THE INVENTION

Accordingly, one aspect of the present invention is to provide an improved method for preparing solid phase conjugate vaccines.

Another aspect of the invention is to provide an improved method for purifying a conjugate vaccine containing a carbohydrate.

Another aspect of the invention is to provide an improved method for preparing solid phase conjugate vaccines containing an aluminum solid phase, a protein, and a carbohydrate.

Still another aspect of the present invention is in providing an improved method for preparing a solid phase conjugate vaccines containing a hapten.

Additional aspects of the invention will be set forth in part in the description that follows, and in part will be apparent from the description, or may be learned by the practice of the invention. The aspects of the invention will be realized and attained by means of the elements and combinations particularly pointed out in the appended claims.

The present invention provides a novel method to prepare solid phase conjugate vaccines, wherein a protein is first adsorbed to a solid phase adjuvant and an oligosaccharide or polysaccharide is then covalently linked to the adsorbed protein.

The present invention further provides a novel method wherein a carbohydrate is first adsorbed to a solid phase adjuvant and a protein is then covalently linked to the adsorbed carbohydrate.

The present invention still further provides a method wherein the carbohydrate is activated prior to coupling to the protein.

The present invention still further provides a method to prepare solid phase conjugate vaccines, wherein a hapten is bound to a protein.

The simple, low cost process eliminates the need for chromatography and allows the rapid removal of unconjugated carbohydrate, which has been shown to inhibit the immune response.

Both the foregoing general description and the following detailed description of the invention are exemplary and explanatory only and are not restrictive of the claimed invention.

DETAILED DESCRIPTION OF THE INVENTION

Solid phase chemistry, a process in which the chemistry is performed on molecules tethered to macromolecular surfaces, is well-known in the art. G. B. Fields & S. P. Colowick, Ed., "Solid Phase Peptide Synthesis," *Meth. Enzym.*, Vol. 289, Academic Press, 1997. In solid phase synthesis, reagents are easily removed, and the product obtained, by simple washing steps.

In the preparation of vaccines for human vaccines, the removal of the vaccine product from the solid phase, which is typically a polymeric support, is problematic. A solution to this problem is to use, as the solid phase, material suitable for immunogens, such as aluminum adjuvants. Aluminum adjuvants are the only adjuvants approved for pediatric use.

Applicant has developed an improved process for the synthesis of protein-polysaccharide conjugate vaccines, in which macromolecules, more particularly polysaccharides, not haptens, are covalently linked to the adsorbed protein. Since even very high molecular weight polysaccharides will not pellet at low speed, the unconjugated polysaccharide is easily separated from the adsorbed conjugate by centrifugation. This provides an easy and low cost solution to the otherwise difficult removal of unconjugated polysaccharide. As described above, the unconjugated but adsorbed protein may not need to be removed and may, in fact, be beneficial for enhancing the antibody response to the protein component.

Current FDA specifications do not require that the free protein be removed from conjugate vaccines, but do set the allowable amount of free polysaccharide. Free polysaccharide, especially when greater than 10% of the total, has been shown to inhibit the humoral immune response to the conjugated polysaccharide. Peeters. C. et al. *Vaccine*, 10:833, 1992. It is, therefore, important that the amount of free polysaccharide in the final product be minimized. However, removal of the free polysaccharide is difficult by gel filtration, particularly when the polysaccharide is of high molecular weight.

The solid phase coupling method allows for the preparation of protein-polysaccharide conjugates with otherwise difficult proteins that are either poorly soluble or difficult to prepare as concentrated solutions. For conjugation of most macromolecules, it is important to have a high concentration of the components. The solid phase method makes this achievable with otherwise difficult proteins, as the adsorbed protein can easily be concentrated. For example, F protein (isolated from Respiratory Syncytial Virus) was not easily concentrated and was soluble only in detergent. To date, the F protein has not been linked in a dilute detergent solution to a polysaccharide by conventional means. However, it is possible to adsorb the F protein to ALHYDROGEL and then covalently link polysaccharide to the adsorbed protein.

Proteins adsorb to aluminum adjuvants via both hydrophobic and ionic interactions. Al-Shakhshir R. H. et al., *Vaccine* 13:41, 1995. Binding is often optimal near the isoelectric point of the protein. Due to the mixed mode of the interaction, the adsorption of proteins cannot be predicted with certainty and optimal conditions must be determined experimentally. The binding is sometimes reversible. Thus, it is necessary to use a chemistry which does not use conditions which desorb the protein, or in which the protein can be readily readsorbed to the adjuvant.

The protein is not particularly limited. Examples of suitable proteins include, but are not limited to, viral, bacterial, parasitic, animal and fungal proteins or lipoproteins.

Preferably, the protein albumin (such as bovine serum albumin), F protein, tetanus toxoid, diphtheria toxoid, or bacterial outer membrane protein, all of which may be obtained from biochemical or pharmaceutical supply companies or prepared by standard methodology (Cruse, J M (ed.) *Conjugate Vaccines in Contributions to Microbiology and Immunology,* vol. 10 (1989), specifically incorporated herein by reference). Other suitable proteins would be known to those of ordinary skill in the art of immunology.

Preferably, the carbohydrate is an oligosaccharide or polysaccharide. Examples of suitable carbohydrates include, but are not limited to, neutral polysaccharides, such as pneumococcal type 14 capsular polysaccharide (Pn14), and dextran, and charged polysaccharides, such as Neisseria PsC, pneumococcal polysaccharide type 6 (Pn6).

Preferably, the carbohydrate is activated. The activator is not particularly limited. Examples of suitable activators include, but are not limited to, CDAP (1-cyano-4-dimethylaminopyridine tetrafluroborate) and cyanogen bromide. Protein can be directly added to the activated polysaccharide, simplifying the chemical linking of the two components. Lees, A. et al., *Vaccine,* 14:190, 1996; see also U.S. Pat. Nos. 5,651,971 and 5,693,326. Preferably, the activator is CDAP. Various chemistries allow for the coupling of proteins to carbohydrates, either with or without a spacer.

The aluminum adjuvant is not particularly limited. In general, metal salts may be used, e.g., aluminum and calcium salts. Examples of suitable activators include, but are not limited to, alum (potassium aluminum sulfate), aluminum hydroxide, aluminum phosphate, aluminum oxohydroxide, aluminum hydroxyphosphate, calcium phosphate, cerium nitrate, zinc sulfate, colloidal iron hydroxide, and calcium chloride. Several aluminum adjuvants with different physical properties are commercially available and approved for human use. Preferably, the adjuvant is aluminum hydroxide or aluminum phosphate. R. H. Al-Shekhshir, et al., *Vaccine,* Vol. 13, 41; (1995); R. K. Gupta, et al., *Vaccine,* Vol. 11, 293 (1993), M. F. Powell, et al., "Vaccine Design, the Subunit and Adjuvant Approach," *Pharmaceutical Biotech,* Vol. 6, Plenum Press (1995). ALHYDROGEL (aluminum hydroxide) with an isoelectric point ($P_i$) of 11, readily adsorbs many proteins with a low $P_i$ such as tetanus toxoid and BSA but not basic proteins such as lysozyme. Adjuphos (aluminum phosphate), with a $P_i$ of 5, binds lysozyme but not BSA. Al-Shakhshir R. H. et al., *Vaccine* 13:41, 1995. The isoelectric point of ALHYDROGEL can be reduced by the addition of phosphate, which increases the negative charge of the adjuvant and permits the adsorption of more basic proteins. Rinella Jr. J. V. et al., *Vaccine* 14:298, 1996.

Neutral polysaccharides, such as pneumococcal type 14 capsular polysaccharide (Pn14) and dextran, are not readily adsorbed to ALHYDROGEL. Therefore, these unconjugated polysaccharides are easily removed from the conjugate by repeated centrifugation and resuspension of the solid phase.

Charged polysaccharides, such as pneumococcal polysaccharide type (Pn6), may be adsorbed to the adjuvant. For such polysaccharides, it will be necessary to determine conditions under which there is minimal adsorption of free polysaccharide. This may be done by modifying the surface charge of the solid phase adjuvant with phosphate anion, which lowers the isoelectric point of the adjuvant. Rinella Jr. J. V. et al., *Vaccine* 14:298, 1996; Chang M. et al., *PDA J. Pharm. Sci Tech.,* 51:25, 1997.

Another potential problem with the solid phase method is that the crosslinking conditions must be carefully controlled to prepare a homogenous product. In solution phase, high levels of crosslinkinig may lead to a more viscous but still usable product. In the solid phase, overcrosslinking can lead to clumping, making it difficult to administer uniform doses. Thus, optimization of the conjugation conditions, e.g., degree of chemical activation of the polysaccharide and concentration of the protein, is necessary.

In a preferred embodiment, solid phase adjuvant methodology is used to synthesize a hapten-protein-polysaccharide conjugate.

In another preferred embodiment, haptens are coupled to high molecular weight protein-polysaccharide conjugates to stimulate enhanced antibody responses to all three components of the vaccine: hapten, protein and polysaccharide. The protein and hapten are presented in a multivalent array on the polysaccharide, thus leading to enhanced B cell activation and consequently enhanced antibody secretion. This is a "dual conjugate vaccine," in that it consists of hapten-protein-high molecular weight polysaccharide. Lees et al., *Vaccine,* 12:1160, 1994; U.S. Pat. No. 5,585,100.

In another preferred embodiment, moieties may be further conjugated to one or more of the protein or polysaccharide components. Such conjugation promotes enhanced antibody responses to the moiety. Techniques to conjugate such moieties are well known to those skilled in the art, and include, in part, coupling through available functional groups (such as amino, carboxyl, thio and aldehyde groups). See S. S. Wong, *Chemistry of Protein Conjugate and Crosslinking,* CRC Press (1991), and Brenkeley et al., "Brief Survey of Methods for Preparing Protein Conjugates With Dyes, Haptens and Cross-Linking Agents," *Bioconjugate Chemistry* 3:1 (January 1992), G. T. Hermanson, *Bioconjugate Techniques,* Academic Press, (1996), all of which are specifically incorporated herein by reference. As used herein, moiety is any substance that is able to stimulate the immune system either by itself or once coupled. Moieties include haptens, antigens, or combinations thereof.

Haptens refer to small organic molecules, e.g., peptides, phosphorylcholine, and TNP, that by themselves are not able to elicit an antibody response, but can elicit an antibody response once coupled to a carrier. An antigen is any molecule that, under the right circumstances, can induce the formation of antibodies. These hastens and antigens may derive from but are not limited to bacteria, rickettsiae, fungi, viruses, parasites, drugs, or chemicals. They may include, for example, small molecules such as peptides, oligosaccharides (for example, the polyribosyl-ribitol-phosphate of *H. influenzae*), toxins, endotoxin, etc.

The solid phase adjuvant approach is well-suited to the preparation of dual conjugate vaccines as sequential conjugation chemistry can be performed on the adsorbed protein, and the separation of unreacted components from the adsorbed conjugate is readily accomplished. Thus, the adsorbed protein can be labeled with hapten, either before or after it is coupled to the polysaccharide. However, charged haptens may bind nonspecifically to some adjuvants. As with charged polysaccharides, this may be overcome by modifying the surface charge of the adjuvant, or by selection of a more suitable solid phase, as a skilled artisan can readily determine. One example of a solid phase adjuvant is a particle with immune-enhancing properties.

In a preferred embodiment, a solid phase adjuvant is used to synthesize hapten-protein-polysaccharide conjugates, using antigens which have been shown to contain important protective epitopes for *S. pneumonia.*

Pneumococci possess, in addition to type specific capsular polysaccharides, a number of antigens common to the species. Phosphorylcholine (PC) is a major determinant of the C polysaccharide of pneumococci, and antibodies to PC have been shown to protect mice from experimental pneumococcal infection. Wallick, S. et al., *J. Immunol.*, 130:2871, (1983); McDaniel L. S. et al,. *J. Immunol.*, 133:3308, (1984).

Pneumococcal surface protein A (PspA) is a surface exposed virulence factor that has been shown to elicit protective immunity to pneumococcal sepsis in mice and can elicit protection against pneumococci of different capsular types. Wu, H-Y et al., *J. Infec. Dis.*, 175:839, 1997.

The invention also relates to the treatment of a patient by administration of an immunostimulatory amount of the vaccine. A patient is any subject for whom the treatment may be beneficial and includes, but is not limited to, mammals, preferably humans, horses, cows, dogs, and cats as well as avians, such as chickens.

An immunostimulatory amount refers to that amount of vaccine that is able to stimulate the immune response of the patient for the prevention, amelioration, or treatment of diseases. The vaccine of the invention may be administered by any route, but is preferably administered by intravenous, intramuscular, and subcutaneous injections.

The invention also relates to a method of preparing an immunotherapeutic agent against infections caused by bacteria, viruses, parasites, fungi, or chemicals by immunizing a host with the vaccine described above so that the donor produces antibodies directed against the vaccine. Antibodies would be isolated or B cells may be obtained to later fuse with myeloma cells to make monoclonal antibodies. The method of making monoclonal antibodies is well known in the art, Kohler and Milstein, *Nature* 256:495 (1975), specifically incorporated herein by reference, and needs no further description here.

As used herein, immunotherapeutic agent refers to a composition of antibodies that are directed against specific immunogens for use in passive treatment of patients. A plasma donor is any subject that is injected with a vaccine for the production of antibodies against the immunogens contained in the vaccine.

The invention also relates to a method of treating a patient by the administration of a protective amount of the immunotherapeutic agent. Such a treatment is passive in that it does not call on the patient to produce antibodies against an immunogen, but rather uses antibodies produced by the plasma donor against the immunogen. The amount of therapeutic antibodies is protective if it presents a sufficient number of antibodies that can prevent, ameliorate, or treat the disease caused by the immunogen. Such an amount may be determined by those of ordinary skill in the art and varies based on the characteristics of the patient and the disease profile.

The invention also relates to a method of producing a diagnostic and/or research reagent to detect agents that are characteristic of diseases caused by, for example, bacteria, viruses, fungi, parasites or chemicals by immunizing a host with a vaccine described above so that the host produces antibodies (or B cells) against the agents. The antibodies and/or B cells may be isolated as described above. As used herein, diagnostic reagent refers to a composition of antibodies (polyclonal or monoclonal) that may be used to detect agents that are characteristic of diseases. As used herein, research reagent refers to a composition of antibodies (polyclonal or monoclonal) that may be used in the laboratory.

METHODOLOGY

Figure 4:
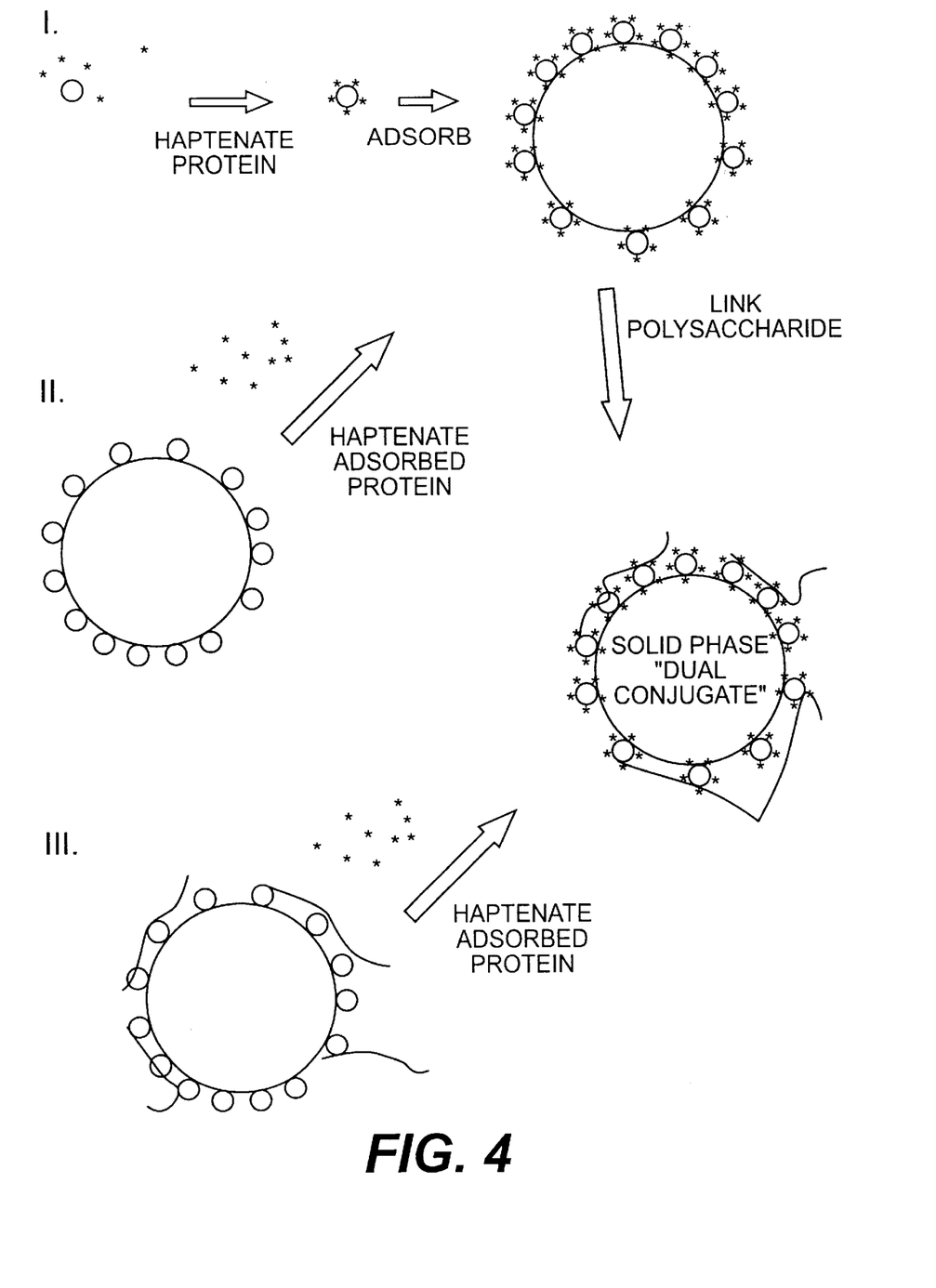
FIG. 4 illustrates three pathways for the preparation of a dual conjugate vaccine.

The overall process for preparing a solid phase conjugate is illustrated in FIG. 4.

Reagents

Pneumococcal types 6B and 14 are available from the ATCC. Tetanus toxoid is available from the Statens Seruminstitute (Denmark). Stabilized aluminum adjuvants, ALHYDROGEL (aluminum hydroxide) and Adjuphos (aluminum phosphate) are available from Accurate Chemical (Westbury, N.Y.). The phosphorylcholine analogue, 6-(O-phosphorylcholine)hydroxyhexanoic acid (PC-$CO_2$H), prepared by the method of Spande was a gift of J. Kenny, (National Institute on Aging, NIH). Spande, T. F., *J. Org Chem.*, 45:3081, (1980).

Recombinant pneumococcal surface protein A (rPspA), consisting of the N-terminal 290 amino acids and a 6×His C terminal, was grown in yeast cells as described by Wortham et al., *Infect. Immun.*, 66:1513, 1998. Following initial purification by Ni-NTA chromatography (Qiagen), the protein may be further purified by ion exchange chromatography as follows: the Ni-NTA fraction is dialyzed into 5 mM TrisHCl+15 mM Tris and loaded onto a Mono Q column equilibrated with the same buffer. The salt is stepped to 50 mM NaCl and the protein eluted during a 50 mM–0.4 M NaCl gradient. The rPspA peak, determined by ELISA, is pooled and concentrated by ultrafiltration to 5 mg/ml, exchanged into saline and sterile filtered with a Millex GV 0.2$\mu$ filter. Purity was confirmed by SDS-PAGE. The concentration is determined from the calculated extinction coefficient of 7620 $M^{-1}$.

Adsorption of Proteins to Solid Phase Adjuvants

Figure 2:
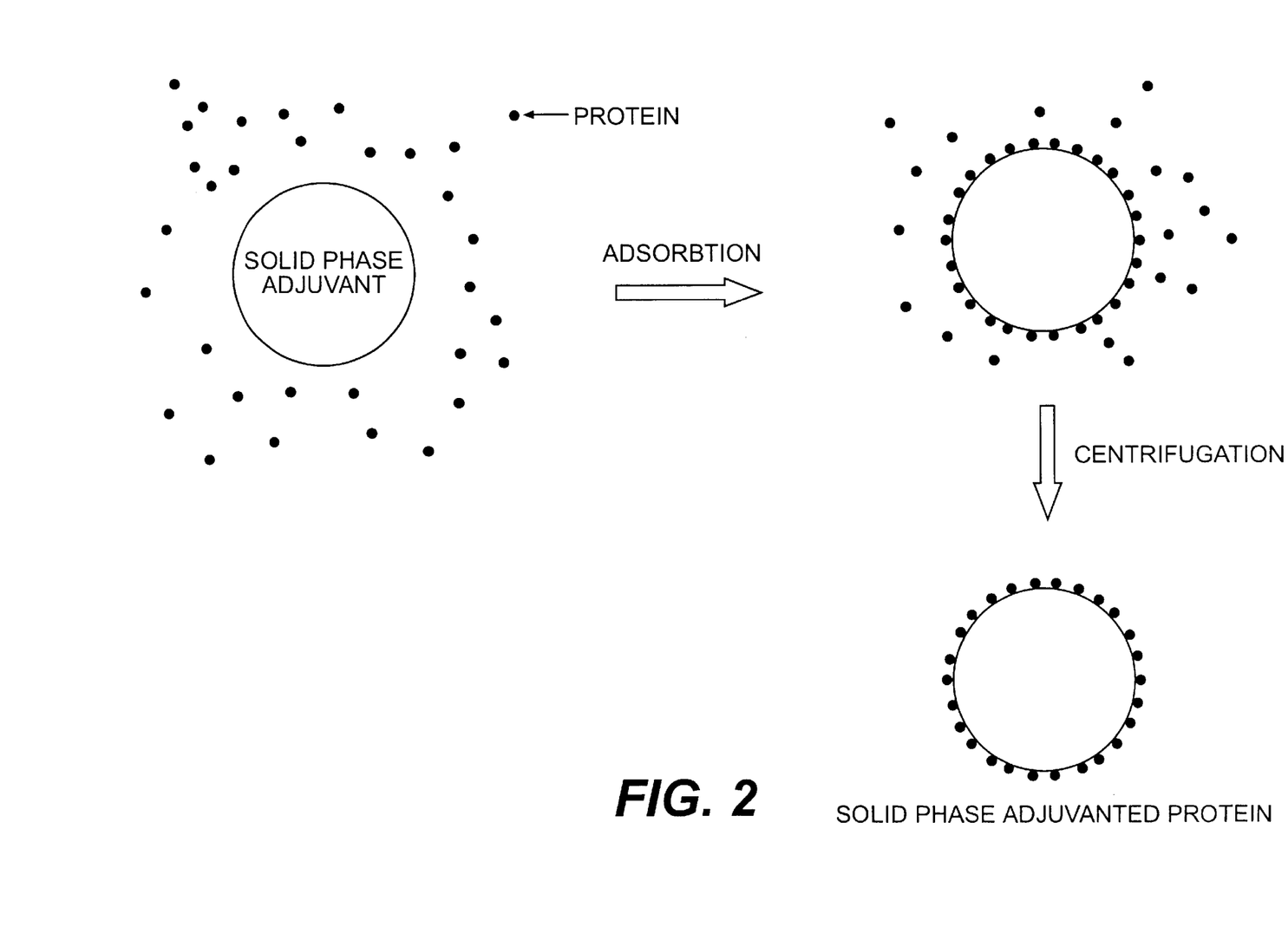
FIG. 2 illustrates the step of adsorbing a protein to a solid phase adjuvant, followed by centrifugation to yield the solid phase adjuvanted protein.
Figure 3:
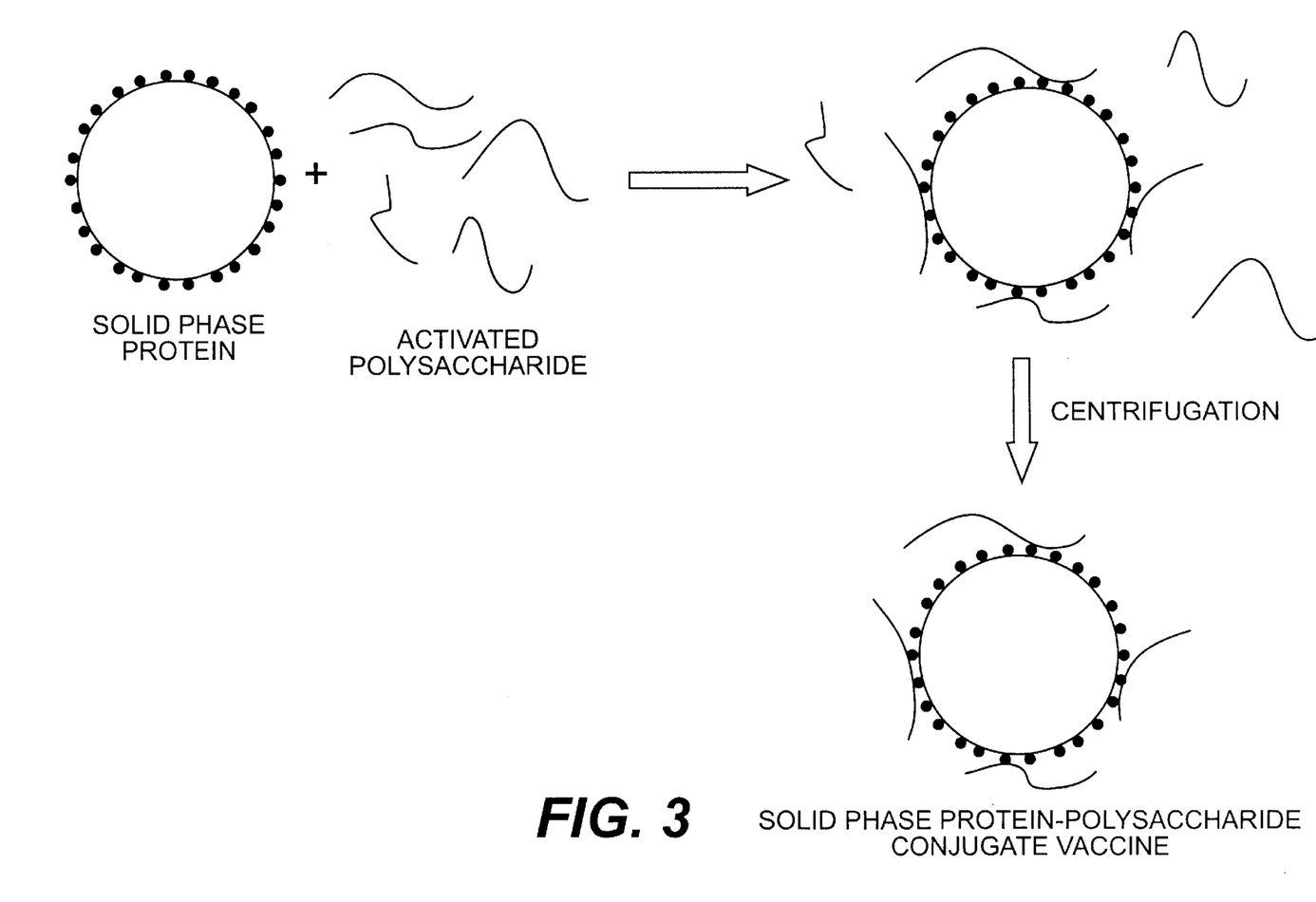
FIG. 3 illustrates the step of conjugating activated polysaccharide to a solid phase protein, followed by centrifugation to remove the excess activated polysaccharide to yield a solid phase protein-polysaccharide conjugate vaccine.

The standard procedure for adsorption of proteins to ALHYDROGEL is as follows, as generally illustrated in FIG. 2. BSA was adsorbed to ALHYDROGEL as generally described by Houen et al., "Conjugation to Preadsorbed Preactivated Proteins and Efficient Generation of Antipeptide Antibodies," *J. Immunol. Meth.*, 206: 125–134, (1997). BSA was first adsorbed to the aluminum adjuvant, ALHYDROGEL by combining, 4.2 ml of BSA (50 mg/ml in saline) with 23 ml of ALHYDROGEL (1:2 dilution in saline) and gently mixed overnight by rotation in a 50 ml tube. The adsorbed protein was washed three times by centrifugation at 3200×g for 10 minutes and resuspended in saline. The final pellet was resuspended in 10 ml of saline+0.02% azide and stored at 4° C. The absorbed BSA was assayed using the microBCA assay (Pierce Chemical) with soluble BSA as the standard. It was found that >95% of the BSA was with the solid phase adjuvant.

Tetanus toxoid (5 mg/ml) was dialyzed into 10 mM MES, 0.15 M NaCl, pH 6. rPspA (5 mg/ml) was dialyzed into 50 mM sodium acetate, pH 5. The protein was mixed with 1% ALHYDROGEL and gently agitated for 1 hour at room temperature. The solid phase adjuvant adsorbed protein was centrifuged for 15 minutes in 1.5 ml tubes in a microfuge at 16,000×g and the supernatant removed. The pellet was resuspended in 1 ml of 25 mM sodium acetate, pH 5 using a microhomogenizer (Kontes "PELLET PESTLE") and recentrifuged. The washing steps were repeated 2 more times and the adsorbed protein resuspended in the final buffer. To vary the density of adsorbed protein, ratios of 0.25–5 mg ALHYDROGEL per mg protein may be used. At 1 mg protein/mg ALHYDROGEL, >90% of the protein was adsorbed. If necessary, the isoelectric point of the ALHYDROGEL may be reduced by the addition of limited amounts of phosphate, as described by Rinella, Jr., J. V. et al., *Vaccine* 14:298 (1996). If ALHYDROGEL proves unsatisfactory for use in preparing solid phase protein-polysaccharide conjugates with negatively charged polysaccharides, such as Pn6, or constructs containing negatively charged haptens, such as phosphorylcholine, the protein may be adsorbed to a solid phase aluminum adjuvant with a low isoelectric point, e.g., Adjuphos. Adjuphos-adsorbed protein and conjugates are resuspended in a 25 mM pH 9 carbonate buffer, instead of the 25 mM sodium acetate buffer used with ALHYDROGEL.

Protein was assayed using the BCA microassay (Pierce Chem. Co.). Using the test protein, BSA, and "bookkeeping" of all fractions, we have determined that adsorbed protein can be quantitated with this method.

Polysaccharide was assayed with the resorcinol/sulfuric acid method of Monsigny et al., *Anal. Biochem.*, 175:525 (1988).

General Procedure for CDAP Activation of Polysaccharide (2)

Pn14 was solubilized at 10 mg/ml in water. CDAP (Research Organics) was prepared at 100 mg/ml in acetonitrile. At t=0, CDAP was added at to PS. At 30 seconds, 0.2 M triethylamine (TEA) was added to bring the pH to 9.5. The pH was maintained at 9–9.5, and at 2.5 minutes, added to a vortexed solution of protein (either soluble or adsorbed). Solid phase conjugates were periodically mixed with a microhomogenizer for the first hour. After an overnight reaction, the solution was quenched by adding ethanolamine to 0.1 M and incubating for 1 hour. Solution phase conjugates were processed by gel filtration on a S400HR column (Pharmacia) to remove unconjugated protein. Unconjugated polysaccharide was removed from adjuvant adsorbed proteins by first making the solution 25 mM in sodium acetate, reducing the pH to 5 with 1 N HCl, and incubating at room temperature for 1 hour. The solid phase conjugate was washed as described. To vary the degree of polysaccharide activation, CDAP ratios of 0.25–1 mg CDAP/mg Ps were tested. To vary the coupling conditions, the adsorbed protein was resuspended at 5, 10 or 20 mg/ml before the addition of the CDAP-activated PS. CDAP-activated Pn14 may be linked to the adjuvant adsorbed PC-rPspA.

In all of the above cases free unconjugated hapten, protein or polysaccharide was removed from the final product by centrifugation and washing of the ALHYDROGEL, which contains the conjugate vaccine. This is the principal time and cost saving step in the preparation of the conjugate vaccines, since column chromatography need not be used for removal of free hapten, protein or polysaccharide.

Immunizations

The following provides an example of how immunizations may be performed in mice. Groups of 5 Balb/c mice are immunized subcutaneously on days 0 and 14 and bled 14 days later with the various vaccine constructs at doses ranging from 0.01–10 μg. To optimize the amount of adjuvant, immunogens are mixed with additional ALHYDROGEL over the range 0–0.5 mg/mouse. As an example of optimizing the amount of additional adjuvants, the solid phase conjugate immunogens are mixed with ALHYDROGEL.

ELISA

All immunoassays are performed using Nunc Maxisorp stripwells (Nunc 469949). Using previously prepared antisera to phosphorylcholine, PspA, tetanus toxoid, Pn14 and Pn6B, preliminary experiments are done to determine the optimal concentration of coating antigen. PC is linked to BSA for use as an ELISA antigens, using the procedure described above. For ELISA's, 100 μl of antigen solution in PBS (pH 7.4) is added to all wells and the plate covered with a plate sealer and incubated overnight at room temperature.

The wells are washed four times with PBS containing 0.05% Tween-20 (PBS-T) to remove unbound coating antigen. Serum samples are tested at 6–7 dilutions, prepared in PBS-T. One hundred μl of each dilution are added to duplicate wells on the antigen-coated plate. Negative control wells receive PBS-T only. Positive control wells are included. For purposes of comparison, each ELISA includes the most recent serum samples as well as the previous serum samples. Following addition of the serum samples, the plate is incubated for 30–60 minutes at room temperature, and the wells washed again with PBS-F. All wells receive 95 μl of rabbit anti-mouse IgG (gamma-specific) conjugated to HRP. The plates are again incubated at room temperature for 30–60 minutes and washed with PBS-T. One hundred μl of TMB substrate will be added to all wells and the plate incubated in the dark at room temperature for 15 minutes. The reaction will be stopped by the addition of 80 μl of TMB Stop Solution and the absorbances determined using a Molecular Devices microplate reader with a 450 nm filter. Titers are calculated using the SoftMax program. Specificity of anti-PC antibodies are confirmed by preincubation of the antibody with 100 μg/ml of phosphorylcholine (Aldrich) and blocking of the antibody binding to PC-BSA are determined.

In selected instances the protective activity of the sera is evaluated using an opsonic assay. Fischer, G W et al., *J. Infect. Dis.*, 169:324 (1994). The skilled artisan will appreciate that the methodology for the preparation of solid phase protein-polysaccharide conjugates may require optimization for a given conjugate such as PC-PspA-Pn6. For example, it may be necessary to modify the conditions to prevent nonspecific adsorption of PC and Pn6. Thus, if reducing the positive charge of the Alhdrogel by adsorption of limiting quantities of phosphate does not prevent nonspecific binding or if we are unable to adsorb PspA to charged Adjuphos, the isoelectric point of the PspA may be raised by genetically engineering a polylysine tail at the C-terminal, to promote binding of the protein to Adjuphos, which has an isoelectric point of about 5. The negatively charged Adjuphos should not bind anions.

EXAMPLES

A. Preparation of Solid Phase Conjugate Vaccine

These examples demonstrate the conjugation procedure on a solid phase matrix and examine some of the parameters that are important for the coupling of high molecular weight polysaccharides (Ps) to solid phase, adjuvant-adsorbed protein. BSA was used as a representative protein and was adsorbed to the commercial solid phase aluminum hydroxide adjuvant, ALHYDROGEL, as described by Houen, G. et al., *J. Imm. Meth.*, 206:125, 1997. The polysaccharide was activated with 1-cyano-4-dimethylaminopyridine tetrafluroborate (CDAP), as generally described by Lees et al., *Vaccine*, 14:190 (1996) and then coupled to the adsorbed protein as described below.

Example 1

Effect of polysaccharide activation and coupling pH on the efficiency of conjugation to protein adsorbed on a solid adjuvant matrix.

*S. pneumoniae* polysaccharide type 14 (Pn14) (3 mg at 10 mg/ml) was activated with 0.25, 0.5 or 1 mg CDAP/mg polysaccharide and a 2× molar amount of triethylamine (TEA) and added to 3 mg of BSA/ALHYDROGEL suspended in 100 μl of 0.1 M sodium borate, pH 9.3. After an overnight incubation while mixing, the solutions were quenched with ethanolamine and washed by centrifugation to remove unconjugated polysaccharide. Protein was assayed using the BCA microassay (Pierce Chemical Co.) and polysaccharide was assayed with the resorcinol/sulfuric acid method of Monsigny et al., *Anal. Biochem.*, 175:525 (1988). As indicated in Table 1, the greater the amount of CDAP used, the greater was the extent of Ps coupling to the adsorbed protein.

The reaction was also carried out in a HEPES buffer at pH 7.3. As shown in Table 1, coupling efficiency of the Ps to the protein was significantly lower at pH 7.3.

This experiment demonstrates that CDAP-activated polysaccharides will react with the adjuvant-adsorbed protein and that the degree of CDAP activation and pH of coupling influence the extent of coupling efficiency in a manner similar to solution phase reactions. Lees, A. et al. *Vaccine*, 14:190 (1996).

TABLE 1

Effect of polysaccharide activation and coupling pH on protein conjugation efficiency.

| Coupling pH | mg CDAP/mg Pn14 | (PS-protein conjugate) mg Pn14/mg BSA |
|---|---|---|
| 9.3 | 1 | 0.93 |
| 9.3 | 0.5 | 0.69 |
| 9.3 | 0.25 | 0.46 |
| 7.3 | 1 | 0.49 |
| 7.3 | 0.5 | 0.28 |

Example 2

Figure 1:
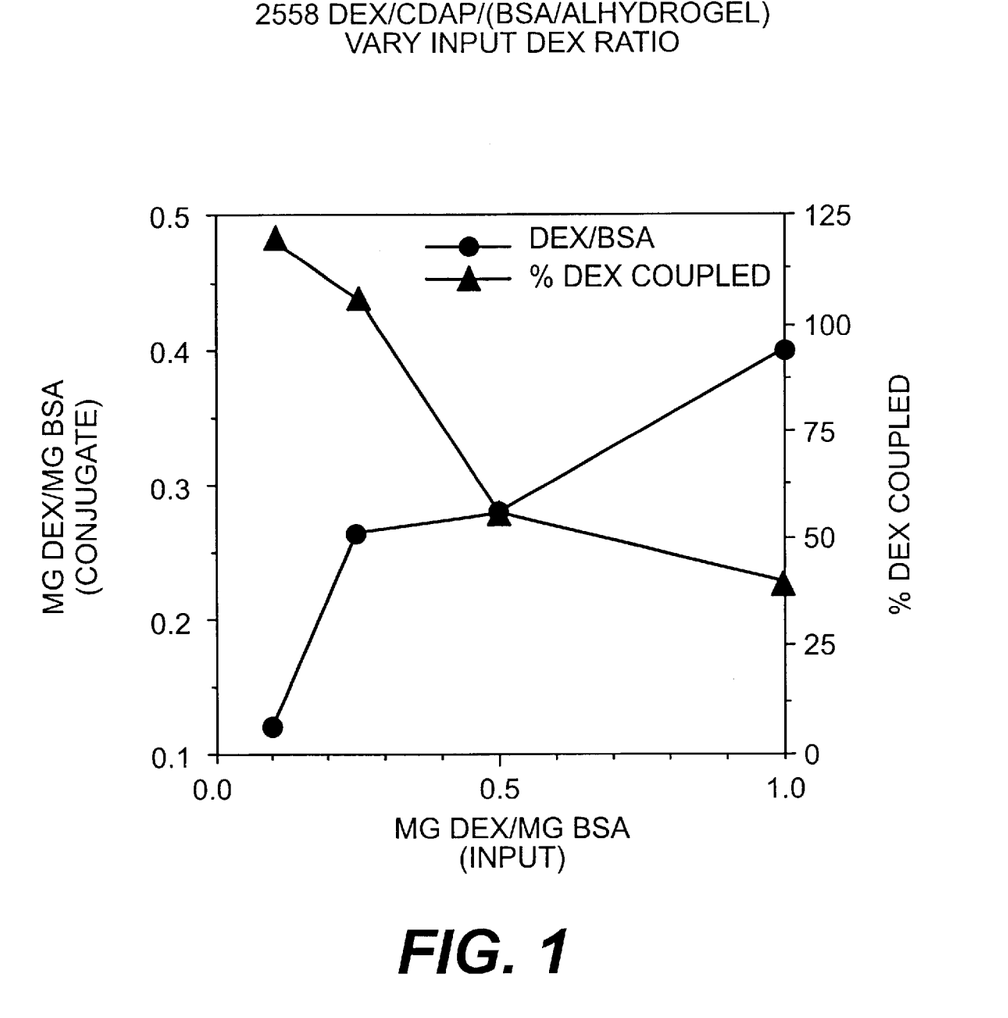
FIG. 1 is a graphical representation of the effects of varying the polysaccharide/protein ratio.

Effect of varying the polysaccharide/protein input ratio. BSA was adsorbed to ALHYDROGEL and CDAP-activated dextran prepared as described above and added to the adsorbed protein at the ratios indicated in FIG. 1. As the amount of dextran relative to BSA was increased, there was a decrease in the percentage of dextran that was conjugated, but an overall increase in the absolute amount of dextran that was conjugated (FIG. 1). This demonstrates that the ratio of polysaccharide to protein can be varied by varying the input PS/protein ratio.

Example 3

Unconjugated, neutral polysaccharide is not adsorbed to ALHYDROGEL.

Three mg of dextran or CDAP-activated dextran at 10 mg/ml was added to 3 mg of ALHYDROGEL-adsorbed BSA at 10 mg/ml in 5 mM sodium borate, pH 9.3. After an overnight reaction, the pH was reduced to 5 by adding 1 M sodium acetate. The solid phase material was centrifuged and resuspended three times in 1 ml of 50 mM sodium acetate (pH 5).

Recovery of protein and polysaccharide was determined. As shown in Table 2, very little, if any, dextran was adsorbed to the solid phase protein unless the dextran was activated with CDAP. This experiment also indicates the excellent recovery of the conjugate that is achievable by the solid phase methodology. Similar results were obtained with Pn14.

TABLE 2

Polysaccharide adsorption to ALHYDROGEL.

| | % recovery | | |
|---|---|---|---|
| | Dextran | BSA | mg Dex/mg BSA |
| Dextran | 1.5% | 98% | <0.02 |
| CDAP-activated Dextran | 29% | 82% | 0.4 |

Example 4

Synthesis of a model conjugate vaccine on a solid matrix and immunization of mice.

BSA was adsorbed to ALHYDROGEL and washed as described above in the Methodology section. Pn14 was activated with CDAP (as described above in the Methodology section) and added to the BSA/ALHYDROGEL. After an overnight reaction, the samples were quenched and washed by repeated centrifugation to remove free Ps. Controls were prepared by mixing Pn14 with ALHYDROGEL ("Alhy."), alone and with adsorbed protein, and by mixing CDAP-activated Pn14 with ALHYDROGEL.

Groups of 4 Balb/c mice were immunized subcutaneously on days 0, 14 and 28 with 2.5 µg of Pn14, either as conjugates prepared by solid phase synthesis or as indicated in Table 3. Mice in the conjugate group received 3 µg BSA. BSA only groups received 5 µg BSA. Sera from a day 42 bleed was titered by ELISA for IgG antibody to Pn14.

This experiment demonstrates that anti-polysaccharide antibodies can be induced using conjugates prepared using a solid phase approach. In the absence of covalent linking of the polysaccharide to the protein, no anti-polysaccharide antibody was detected. Covalent linking of the polysaccharide to the protein only occurs when polysaccharide has been activated, e.g., by CDAP. This experiment did not compare efficacy of conjugates prepared by solid phase vs. conventional methods.

TABLE 3

Immunization of mice by solid matrix conjugate vaccine.

| Immunogen | Anti-Pn14 IgG titer* |
|---|---|
| (Pn14/CDAP)/(BSA/Alhy.) | 7134 |
| (Pn14/CDAP) + Alhy. | 0 |
| (Pn14/CDAP) + Alhy. (washed) | 0 |
| Pn14 + Alhy. | 0 |
| Pn14 + (BSA/Alhy.) | 0 |
| Pn14 | 0 |
| BSA | 0 |
| (BSA/Alhy) | 0 |

*Elisa titer @ 0.5 OD cutoff

B. Antibody Induction

Antigens were used that have been shown to induce protective antibodies for *Streptococcus pneumoniae*. These examples induce protective, high titer protective antibody to *S. pneumoniae* using the proposed vaccine components phosphorylcholine (PC) and pneumococcal surface protein A (PspA).

Example 5

Synthesis of a clinically relevant conjugate vaccine using solid phase adjuvant matrix.

The fusion protein (RSV F protein) was purified from respiratory syncytial virus grown in HEp-2 cells and adsorbed to ALHYDROGEL. The ALHYDROGEL-adsorbed protein was washed by centrifugation to remove nonadsorbed protein and coupled to CDAP-activated Pn14. Unconjugated Pn14 was removed by centrifugation. Groups of 4 Balb/c mice were immunized subcutaneously on days 0 and 14 with 2.0 µg of the F protein Pn14 conjugate prepared on ALHYDROGEL or with 2 µg F-protein adsorbed to ALHYDROGEL plus 5 µg Pn14, comixed with the protein. Additional ALHYDROGEL was mixed with each immunogen so that each mouse received a total of 0.1 mg of ALHYDROGEL per immunization. Anti-F protein and anti-Pn14 ELISA titers were determined on pooled sera from mice bled on day 28.

Pools of the above sera were tested for their ability to promote opsonophagocytosis. Only sera from mice immunized with the conjugated Pn14 were found to have opsonophagocytic activity. This experiment demonstrates that the conjugate vaccine prepared using RSV F protein conjugated to Pn14 using a solid phase system induced high titer antibody to both the Ps and the protein component. In contrast, mice immunized with the solid phase F protein comixed with Pn14 gave no titer to the polysaccharide. Results are shown in Table 4.

TABLE 4

Synthesis of a clinically relevant conjugate vaccine using solid phase adjuvant matrix

| | IgG titer | |
| --- | --- | --- |
| Pn14 plus F protein | Anti-F | Anti-Pn14 |
| Comixed | 75,885 | 6 |
| Conjugated | 59,503 | 10,945 |

Example 6

Induction of high titer anti-phosphorylcholine (PC) antibodies that are protective.

To study whether we could induce high titer and protective antibody to PC, we conjugated a PC analogue to tetanus toxoid or pertussis toxoid (PC-TT,PC-PT), essentially as described in Methods, and immunized DBA/2 mice with 5 µg of protein. Mice were boosted 14 days later, and day 28 sera was titered for IgG antibodies to PC. As seen in Table 5, the mice were stimulated to produce high titer anti-PC antibodies after the booster immunization. All of the mice injected with TT or PT conjugates also mounted high titer antibody responses to the carrier molecule (not shown).

TABLE 5

Induction of high titer anti-phosphorylcholine (PC) protective antibodies.

| | IgG anti-PC titer | |
| --- | --- | --- |
| Immunogen | Day 14 (pre-boost) | Day 28 (post-boost) |
| PC-TT | 2,430 | 11,908 |
| PC-PT | 1,644 | 12,007 |

To test whether the anti-PC antibody that was induced by these immunogens was protective, mice were injected with 0.1 ml of test or control sera. 24 hours later, the mice were infected with 20,000 organisms of the WU2 strain of *S. pneumonia*. While all 5 of the control mice injected died within 72 hours, none of the mice that were given anti-PC containing serum died. This demonstrates that high titer and protective antibodies can be produced after conjugation of PC to clinically relevant carriers.

Example 7

Induction of antibodies to multiple *S. pneumoniae* epitopes.

To determine whether we could conjugate PC to another *S. pneumoniae* protective epitope and induce antibodies to both components, a PC analogue was conjugated to pneumoccocal surface protein A (PspA), as described in Methods and 5.0 µg was injected s.c into 5 DBA/2 mice on days 0 and 14. Mice were bled 14 days later and sera titered for IgG antibodies to both PC and PspA. Five µg PsP-A or 5 µg PsPA are either soluble or mixed with ALHYDROGEL. The data in Table 6 demonstrates that we can induce high titer IgG antibodies to both the PC and the PspA components of the vaccine.

TABLE 6

Induction of antibodies to multiple *S. pneumoniae* epitopes.

| Immunogen | Anti-PspA | Anti-PC |
| --- | --- | --- |
| PspA (in solution) | 27,927 | <100 |
| PspA-PC (in solution) | 27,441 | 23,153 |
| PspA-PC (mixed with ALHYDROGEL | 123,918 | 11,589 |

Example 8

Conjugates containing unconjugated protein are immunogenic and protective.

TT was conjugated to Pn14 using CDAP and the free protein removed by gel filtration on an S400HR column. Another aliquot of the same conjugate was only dialyzed (cutoff 14 kDa) and contained about 50% unconjugated TT (determined by size exclusion HPLC). Recovery of polysaccharide was markedly higher for the dialyzed-only sample than for the gel filtered sample (>95% vs. 37%). Groups of 4 mice were immunized with each preparation on days 0 and 14 and bled 14 days thereafter. Anti-IgG titers were determined by ELISA. Both anti-protein and anti-Ps antibody titers were higher for the dialyzed only formulations.

TABLE 7

Effect of unconjugated protein.

| | Anti-Pn14 IgG titer[a] | | Anti-TT IgG titer[b] | |
| --- | --- | --- | --- | --- |
| Dos | gel filtr | dialy | gel filtr | dialy |
| 10µ | 85.2 | 102.2 | 12.7 | 17.4 |
| 1µ | 33.9 | 69.8 | 5.10 | 7.50 |
| 0.1µ | 22.5 | 67.8 | 4.89 | 7.88 |

[a]0.1 OD ELISA cutoff
[b]0.5 OD ELISA cutoff
[c]based on Pn14

The data suggests that homologous unconjugated protein, present with conjugated protein, stimulates the immune response more than conjugates from which the free protein has been removed. Thus, the presence of unconjugated, adsorbed protein in the solid phase protein-polysaccharide immunogens provides enhanced immune response over that of conventional preparations.

Example 9

Immunogenicity of TTPS conjugates prepared using solid phase adjuvant with various Ps and linking chemistries.

TT was absorbed to ALHYDROGEL and coupled to either Pn14 or Neisseria PsC. Pn14 was activated with CDAP, coupled using thio-ether chemistry or haloacyl conjugation. The thio-ether chemistry method is discussed generally in Lees, *Vaccine*, 12:1160 (1994). The haloacyl conjugation is described in, for example, Lees et al., *Abstract for 11th Int. Pathogen. Neisseria Conf.*, Nice, France, p. 161 (1998). Following conjugation, free Ps was removed by centrifugation and the solid phase conjugate assayed for Ps and TT Groups of 4 Balb/c mice were immunized with 5 μg of conjugated Ps containing the indicated amount of TT, on day 0 and 14 and bled 14 days later. Pooled sera from the day 28 bleed was assayed by ELISA for the homologous Ps and for TT.

TABLE 8

Effect of varying Ps and linking chemistry.

| Chemistry; PS | mg PS/mg TT | dose TT | IgG titer* anti-PS | anti-TT |
|---|---|---|---|---|
| CDAP; Pn14 | 0.22 | 23 μg | 5503 | 23418 |
| Thio-ether; Pn14 | 0.13 | 39 μg | 2111 | 40810 |
| Haloacyl; Pn14 | 0.14 | 35 μg | 748 | 35047 |
| Haloacyl; PsC | 0.58 | 8.8 μg | 25013 | 15785 |

*ELISA cutoff 0.1 OD for Ps and 0.5 for TT.

This demonstrates that the method is suitable for a variety of different chemistries, proteins, and polysaccharides. Note that the haloacyl/PsC conjugate gave a high anti-PsC response, consistent with results absence with solution phase TT-(haloacyl)-PsC conjugates. Note that no effort was made to optimize the conjugation protocol or the dose. The purpose of this experiment was to show that using a variety of chemistries, polysaccharides could be coupled and used to induce antibodies. Furthermore, no comparison could be made between anti-PsC and Pn14 titers.

The following four examples demonstrate preparation of dual conjugate vaccines. Further reference may be made to U.S. Pat. No. 5,955,079, the disclosure of which is incorporated by reference in its entirety.

Example 10

Conjugating Ps to adjuvant-adsorbed hapten-protein (generally described in FIG. 4(II)).

Tetanus toxoid (TT) was adsorbed to ALHYDROGEL as described above, and resuspended at 5 mg/ml in HEPES buffer, (0.15 M HEPES, 2 mM EDTA, pH 7.3). N-hydroxysuccinimidyl iodoacetate (SIA) was added from at 0.1 M stock in dimethylformamide at a 10 fold molar ratio of SIA to TT and reacted in the dark. After one hour, the TT was washed by centrifugation with HEPES buffer to remove unreacted reagent. The iodoacetylated, adsorbed TT was resuspended in HEPES buffer at 10 mg/ml.

A consensus peptide derived from entertoxigenic *E. Coli* (F J Cassels et al. *J. Industrial Microbiology and Biotechnology* 19:66 (1997) (CVEKNITVTASVDPTIDLLQADGSALPSAVALTYSPAG (SEQ ID NO: 1)) was solubilized at 10 mg/ml in HEPES buffer+10% acetonitrile. The free thiol content was determined using Ellman's reagent.

Peptide is added to the iodoacetylated, adsorbed TT at a ratio of 10 moles of free thiol per mole of TT. After an overnight reaction, the solution is made 0.2 mM in mercaptoethanol for one hour and then washed by repeated centrifugation and resuspension in HEPES buffer. The final concentration of TT is 10 mg/ml.

Pn14 at 10 mg/ml is activated with CDAP and coupled to the adsorbed peptide/TT as described in other examples.

Alternatively, peptide is coupled to adsorbed protein as generally described by Houen et al. Ps is coupled to the adsorbed peptide-protein as described in other examples.

Example 11

Hapten-protein prepared before adsorption to solid phase (generally described in FIG. 4(I)).

TT is suspended in HEPES buffer at 5 mg/ml and reacted with 10 fold molar excess of SIA. After 1 hour, protein is desalted and concentrated using an ULTRAFREE 30 device (Millipore) to 10 mg/ml. Peptide is prepared and added as above. After an ON reaction, solution is quenched with 0.2 mM mercaptoethanol for 1 hour. Unconjugated peptide is removed by gel filtration on an S200HR column (Pharmacia), equilibrated with saline. The peptide-TT fraction is concentrated to 10 mg/ml and adsorbed to ALHYDROGEL.

Pn14 at 10 mg/ml is activated with CDAP and coupled to the adsorbed peptide/TT as described in other examples.

Example 12

Hapten coupled to adsorbed protein-Ps (generally described in FIG. 4(III)).

Pn14 is conjugated to ALHYDROGEL adsorbed TT as described. The adsorbed Pn14-protein is iodoacetylated with SIA as described above. The peptide is prepared as described and added to the iodoacetylated protein/Ps. After an overnight reaction, the solution is quenched with mercaptoethanol and the unconjugated peptide removed by repeated washing by centrifugation.

Example 13

Conjugation of protein to adsorbed polysaccharide.

Certain Ps adsorb well to ALHYDROGEL, e.g., *Neisseria meningiditis* A. (Neiss PsA). Neiss PsA is suspended at 10 mg/ml in water and mixed with an equal weight of Alhdrogel. After 1 hour, non-adsorbed Ps is removed by washing by centrifugation and resuspended at 10 mg/ml in saline.

The adsorbed Ps is activated with CDAP. One mg CDAP per mg of adsorbed Ps from a 100 mg/ml stock of CDAP in acetonitrile. At 30 seconds, the pH is raised to 9.5 and maintained at that pH for an additional 2 minutes, using TEA from a 0.2 M stock. At 2.5 min, TT is added at a ratio of 1 mg TT/mg Ps and the pH immediately adjusted to 9. After a 3 hour reaction, unabsorbed protein is removed by washing/centrifugation. As in other examples, hapten can be added to the protein either before or after coupling to the adsorbed Ps.

Example 14

Solid phase Intimin-polysaccharide conjugates

This example illustrates the adsorption of a protein to ALHYDROGEL and Adjuphos, solid phase aluminum adjuvants with low and high isoelectric point. The example indicates that conjugates with negatively charged polysaccharides, which adsorb to ALHYDROGEL, can be prepared on a protein adsorbed to Adjuphos. The conjugates induced an anti-polysaccharide an immune response in mice.

Intimin is a bacterial protein which promotes attachment to the intestinal epithelium and is a virulence factor for EHEC O157:H7 strains, among others. Intimin has an isoelectric point of 9.35 and thus is a basic protein. It has been found that it adsorbs well to both ALHYDROGEL and Adjuphos.

A. Covalent Linkage of Pneumococcal Type 14 Polysaccharide to Intimin Adsorbed to ALHYDROGEL Recombinant Intimin was purified from *E. Coli* (M. L. McKee and A. D. O'Brien, *Infect. Immun.*, 64:2225 (1996) and dialyzed into 20 mM sodium acetate, pH 5.8. 1.4 ml of intimin (~1 mg/ml) was mixed with 1.4 mg of ALHYDROGEL. After 1 hour the adsorbed material was centrifuged and resuspended at 10 mg/ml in 20 mM HEPES, pH 8. Pneumococcal type 14 polysaccharide (Pn14) was activated with 1-cyano-4-dimethylaminopyridine tetrafluoroborate (CDAP) as follows. To 2 mg of Pn14 (10 mg/ml in saline), 50 µl of CDAP (100 mg/ml in acetonitrile) was added. At 30 seconds. 100 µl of 0.2 M triethylamine was added. At 2.5 minutes, the activated Pn14 was mixed with the suspension of Intimin. The mixture was gently agitated for 3 hours and then dialyzed overnight into 20 mM sodium acetate, pH 5.8. The nonadsorbed material was removed by centrifuging and resuspending twice in the same buffer. The final pellet was resuspended in 20 mM sodium acetate to a final volume of 0.64 ml. Using the BCA assay to determine the adsorbed protein and the resorcinol/sulfuric acid assay to determine the polysaccharide, it was found that there was 0.4 mg Pn14 per mg of Intimin.

We found that *Neisseria meningiditis* polysaccharide A (PsA), a negatively charged polymer, was adsorbed to ALHYDROGEL but not to Adjuphos.

One mg PsA (10 mg/ml, water) was mixed with 1 mg Adjuphos (5 mg/ml in 50 mM sodium carbonate, pH 9.3). After incubating for 15 minutes at room temp, nonadsorbed material was removed by centrifuging and resuspending twice in the same buffer. Using the resorcinol/sulfuric acid assay, it was determined that less than 3% of the polysaccharide was adsorbed. When 1 mg of PsA was incubated with 1 mg of ALHYDROGEL in 25 mM sodium acetate, pH 5 and nonadsorbed material removed by centrifuging and re-suspending in the same buffer, more than 25% of the polysaccharide was found adsorbed to ALHYDROGEL. Therefore, Adjuphos would be suitable for preparing solid phase conjugates of negatively charged carbohydrate, as illustrated in the next example.

B. Covalent Linkage of *Neisseria meningiditis* Polysaccharide A to Intimin Adsorbed to Adjuphos A solution of 1 ml of recombinant Intimin (absorbance at 280 nm=1.5) in 20 mM sodium acetate, pH 5.8 was mixed with 2.5 mg of Adjuphos (available from Accurate Scientific, NY) in the same buffer. After 1 hour, the solution was centrifuged and resuspended twice in 20 mM sodium acetate, pH 5.8 and finally resuspended in 100 µl of the same buffer. *Neisseria meningiditis* polysaccharide A (PsA) was hydrolyzed with HCl to about 25 kDa average molecular weight and derivatized on its reducing end with vinylsulfone, as generally described in copending U.S. patent application Ser. No. 08/852,733, filed May 7, 1997, incorporated specifically by reference. Excess reagent was dialyzed away. 2.2 mg of the vinylsulfone-activated PsA in 0.9 ml was combined with the adsorbed Intimin and 100 µl of 1 M sodium carbonate, pH 9 added. After an overnight incubation at 4° C. in the dark, nonadsorbed material was removed by centrifuging and resuspending with saline. The final pellet was resuspended in 0.5 ml 20 mM sodium acetate, pH 5.8. Using assays as above, it was determined that the suspension contained 0.2 mg of PsA per mg of Intimin.

C. Immunogenicity of Intimin-polysaccharide Conjugates Prepared as a Solid Phase on ALHYDROGEL and Adjuphos For comparison, tetanus toxoid was covalently linked to Pn14 and PsA in solution phase reactions. Groups of 4 Balb/C mice are immunized with 2.5 µg of polysaccharide on days 0 and 14. Mice are bled on day 28 and sera assayed for anti-polysaccharide antibodies by ELISA.

TABLE 9

Immunogenicity of Intimin-polysaccharide conjugates.

| | Antibody Titer | |
|---|---|---|
| | Anti-intimin | Anti-Pn14 |
| Intimin-Pn14 (Adsorbed to ALHYDROGEL) | 23,116 | 8,021 |
| | Anti-intimin | Anti-Pn14 |
| TT-Pn14 | — | 9,344 |
| | Anti-intimin | Anti-PsA |
| Intimin-PsA (Adsorbed to Adjuphos) | 4,677 | 5,471 |
| TT-PsA | — | 19,827 |

Example 15

Aluminum Oxide Nanoparticles

A variety of solid phase adjuvanting particles can be used to prepare solid phase protein-polysaccharide conjugate vaccines. Previous examples have employed aluminum hydroxide and aluminum phosphate adjuvants, specifically the commercial products ALHYDROGEL and Adjuphos, respectively. The following examples describe the use of other particles.

Peptides have been covalently linked to functionalized aluminum oxide nanoparticles (0.3 µm diameter) and used as immunogens (Frey et al., *Bioconjugate Chem.*, 8:4204, (1997)). These aluminum oxide nanoparticles are stable, uniform and well characterized. Unlike the aluminum hydroxide and phosphate adjuvants, they don't "age." These properties could be advantageous in producing vaccines. Aluminum oxide particles (0.3µ) derivatized with chloroacetyl groups were a gift from Dr. F. A. Robey of the National Institutes of Health, Bethesda, Md. A process for their preparation is generally described in Frey et al., *Bioconjugate Chem.*, 8:4204, (1997). Non-derivatized aluminum oxide particles were purchased from Fluka (#06280).

Tetanus toxoid (TT) was adsorbed to the aluminum oxide particles as follows: The aluminum oxide particles were suspended in water at 2 g/ml and 3 mg of TT (14.5 mg/ml in 2 M NaCl) added. After a 1 hour incubation, the nonadsorbed material was removed by centrifuging and resuspending in water. 45 mg additional aluminum oxide was mixed with the nonadsorbed TT and it was processed as above. All the adsorbed TT was combined and resuspended in 0.32 ml PBS. By the BCA assay, the sample contained 1.8 mg TT. Three mg of Pn14 (10 mg/ml in water was activated by the addition of 30 μl of CDAP (100 mg/ml in acetonitrile) followed 30 seconds later by the addition of 60 μl of 0.2 M triethylamine. At 2.5 minutes the activated Pn14 was added to the TT adsorbed to the aluminum oxide. After 4 hours, the reaction was quenched by the addition of 100 μl of 1 M glycine, pH 8 and the nonadsorbed material removed by centrifugation and re-suspending in saline. The final conjugate was resuspended in 1 ml saline and determined to contain 0.6 mg Pn14 per mg TT.

As a control, nonactivated Pn14 was mixed with the TT adsorbed to aluminum oxide and processed as above. This prep was called the sham conjugate and contained less than 0.3 mg of Pn14/mg of TT.

TT was covalently linked to chloracetyl-derivatized aluminum oxide nanoparticles as follows: Thiopropyl dithiopyridyl N-hydroxysuccinimide (8 μl of a 10 mM stock) was added to 2 mg of TT (14.5 mg in 2 M NaCl+25 Ml 0.75 M HEPES, 10 mM EDTA, pH 7.3). After 2 hours, 30 μl 1 M sodium acetate (pH 5) was added along with 9 μl of 0.5 M dithiothreitol. After 30 min, the solution was desalted on P6DG column (BioRad), equilibrated with 10 mM sodium acetate, 0.15 M sodium chloride, pH 5. The void volume fraction was concentrated to 230 μl using an ULTRAFREE 30 device (Millipore). It was determined that there were 3.7 mole thiols per mole TT. The thiol-TT was added to a suspension of 50 mg of the activated aluminum oxide suspended in 20 μl 0.1 M EDTA+50 μl 1 M HEPES, pH 8. After an overnight incubation, the resin was washed three times by centrifugation and resuspended in PBS, the final being a volume of 200 μl. The reaction was then quenched by the addition of 4 μl of 10 mM mercaptoethanol. After 30 minutes, the resin was again washed by centrifugation and resuspended in 0.2 ml PBS. Using the BCA assay, it was found that 0.59 mg of TT was conjugated with the resin. Pneumococcal type 14 polysaccharide was activated with CDAP by adding 10 μl of a 100 mg/ml solution of CDAP to 100 μl of a 10 mg/ml solution of Pn14. 30 sec later 20 μl of 0.2 M triethylamine was added. At 2.54 min, the CDAP activated Pn14 was added to the solution of TT covalently linked to the aluminum oxide. After an overnight incubation, the reaction was quenched by the addition of 50 μl of 1 M glycine, pH 8 and washed by centrifugation with PBS and resuspended in 0.2 ml PBS. The product was determined to contain 0.2 mg Pn14 per mg of TT.

Immunogenicity of TT-P14 Conjugates

Groups of 4 BALB/C mice were immunized on days 0 and 14 with 2.5 μg of pneumococcal polysaccharide, either alone or conjugated. For comparison, a solution phase TT-Pn14 conjugate is included. (A second group of mice was similarly immunized. The titer from this experiment is in parenthesis.)

TABLE 10

Immunogenicity of TT-P14 conjugates

| TT-Pn14 conjugate | Anti-Pn14 IgG Antibody Titer |
|---|---|
| Solution phase | 26,027, (9,344) |
| Aluminum oxide (Covalent) | 6,502, (5,225) |
| Nanoparticle (Adsorbed) | 1,383 |
| Sham conjugate | 624 |
| Pn14 only | 758 |

These results indicate that the aluminum oxide resin can be used to prepare protein-polysaccharide conjugates. They also suggest that covalent linkage of the protein to the resin may be superior to adsorption.

The foregoing written description relates to various embodiments of the present invention. Numerous changes and modifications may be made therein without departing from the spirit and scope of the invention as defined in the following claims.

LIST OF REFERENCES (1) Conjugate Vaccines, J. M. Cruse & R. E. Lewis, Jr. Karger, Ed. 1989.
(2) Lees, A. et al. Vaccine 14:190, 1996
(3) M. F. Powell, et al., Vaccine Design, the Subunit and Adjuvent Approach, Pharmaceutical Biotech, Vol. 6, Plenum Press (1995).
(4) Peeters, C. et al. Vaccine 10:833, 1992.
(5) Solid Phase Peptide Synthesis, Meth Enzym. Vol.289 eds G. B. Fields & S. P. Colowick, Academic Press, 1997.
(6) Houen, G. et al. J. Imm Meth 206:125, 1997
(7) Al-Shakhshir R. H. et al. Vaccine 13:41, 1995
(8) Rinella Jr. J. V. et al. Vaccine 14:298, 1996
(9) Chang M. et al. PDA J Pharm Sci Tech. 51;25, 1997
(10) Lees et al. Vaccine 12:1160, 1994
(11a) Wallick, S. et al. J. Immunol 130:2871, 1983
(11b) McDaniel L. S. et al. J. Immunol. 133:3308, 1984
(11c) Briles, D. E. et al. Infect Immun. 60:1957, 1992
(11d) LaFerriere et al. Vaccine 15:179, 1997
(12) Gray, B. M. et al. J. Clin. Microbiol. 18:1102, 1983
(13a) Wu, H-Y et al. J. Infec. Dis 175:839, 1997
(13b) Wortham, C, L. et. al. Infect. Immun. 66:1513, 1998.
(14) Monsigny et al. Anal. Biochem. 175:525, 1988
(15) Spande, T. F., J. Org Chem, 45:3081, 1980
(16) Ames B. N. & D. T. Dubin J. Biol Chem. 235:769, 1960
(17) Lindsberg, M-L. et al. J. Immunol. 147:3774, 1991.
(18) Snapper, C. M. et al. J. Exp. Med. 175:1367, 1992.
(19) Pecanha, L. M. T. et al. J. Immunol. 150:3215, 1993.
(20) Snapper, C. M. et al. J. Immunol. 150:2737, 1993.
(21) Mond, J. J. et al. Ann Rev. Immunol. 13:655, 1995.
(22) Mond, J .J. et al. Current Opinion in Immunol. 7:349, 1995.
(23) Campbell, K. A. et al. Eur. J. Immunol. 22:2107, 1992.
(24) Squire, C. M. et al. J. Imm. 152:4388, 1994.
(25) Campbell, K. A. et al. Int. Immunol 9:1131, 1997.
(26) Lees, A. et al. J. Immunol. 145:3594–3600, 1990.
(27) Morris, S. C. et al. J. Immunol. 149:3836, 1992.
(29) Morris, S. C. et al. J. Imm. 152:3777, 1994.
(30) Finkelman, F. D. et al. J. Imm. 157:1406, 1996.
(31) U.S. Pat. No. 5,585,100.
(32) Cassels, F. J. et al. J. Ind Microbiol Biotech 19:66, 1997.
(33) U.S. Pat. Nos. 5,651,971 and 5,693,326.
(35) Fischer, G W et al. J. Infect. Dis. 169:324, 1994
(36) Kossovsky et al., Bioconj. Chem. 6(5), pp. 507–520 (1995)

What is claimed is:

1. A method for preparing a solid phase vaccine, comprising the steps of:

(a) adsorbing a protein to a solid phase adjuvant; and (b) covalently linking a carbohydrate to the adsorbed protein, wherein both the protein and the carbohydrate are capable of inducing an immune response, and wherein step (a) is performed before step (b).

2. The method according to claim 1, wherein the carbohydrate is an oligosaccharide or a polysaccharide.

3. The method of claim 2, wherein the oligosaccharide or polysaccharide is natural or synthetic.

4. The method according to claim 1, wherein the carbohydrate is Pn14 or Neisseria PsC.

5. The method of claim 1, further comprising the step of activating the carbohydrate prior to step b).

6. The method of claim 5, wherein the activating step is carried out by action of CDAP.

7. The method of claim 1, further comprising the step of adding a hapten to the protein prior to or after step b).

8. The method of claim 1, further comprising the step of purifying the solid phase vaccine by centrifuging, settling, or filtering.

9. The method of claim 1, wherein the protein is a viral, bacterial, parasitic, animal or fungal protein.

10. The method of claim 1, wherein the protein is a F protein, PspA, tetanus toxoid, diphtheria toxoid, bacterial outer membrane protein, viral outer membrane protein, or combinations thereof.

* * * * *

SEQUENCE LISTING

```
<160> NUMBER OF SEQ ID NOS: 1

<210> SEQ ID NO 1
<211> LENGTH: 38
<212> TYPE: PRT
<213> ORGANISM: Escherichia coli

<400> SEQUENCE: 1

Cys Val Glu Lys Asn Ile Thr Val Thr Ala Ser Val Asp Pro Thr Ile
 1               5                  10                  15

Asp Leu Leu Gln Ala Asp Gly Ser Ala Leu Pro Ser Ala Val Ala Leu
            20                  25                  30

Thr Tyr Ser Pro Ala Gly
            35
```